United States Patent

Hwang et al.

[11] Patent Number: 5,430,158
[45] Date of Patent: Jul. 4, 1995

[54] PYRAZOLE DERIVATIVES

[75] Inventors: Ki J. Hwang; Kyung H. Park, both of Daejeon, Rep. of Korea

[73] Assignee: Korea Research of Chemical Technology, Daejon, Rep. of Korea

[21] Appl. No.: 313,975

[22] Filed: Sep. 28, 1994

Related U.S. Application Data

[62] Division of Ser. No. 39,373, Jun. 18, 1993.

[30] Foreign Application Priority Data

Aug. 20, 1991 [KR] Rep. of Korea .................. 91-14311

[51] Int. Cl.$^6$ .................. C07D 231/20; C07D 231/22
[52] U.S. Cl. .................. 548/366.1; 548/371.1
[58] Field of Search .................. 548/366.1, 371.1

[56] References Cited

U.S. PATENT DOCUMENTS 5,185,025 2/1993 Moedritzer et al. ............. 548/366.1

Primary Examiner—Robert W. Ramsuer
Attorney, Agent, or Firm—Kenyon & Kenyon

[57] ABSTRACT

An anilin derivative which corresponds to the following formula:

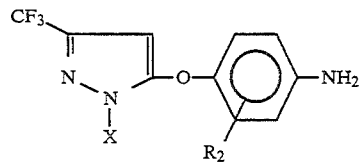

wherein, $R_2$ is hydrogen, lower alkoxy group, a nitro group, or one or more halogen atoms selected from fluorine, chlorine and bromine; and X is a lower alkyl group or a phenyl substituent. The compounds are intermediates for insecticides.

1 Claim, No Drawings

PYRAZOLE DERIVATIVES

This application is a division of U.S. patent application Ser. No. 08/039,373 filed on Jun. 18, 1993.

BACKGROUND OF THE INVENTION

The present invention relates to novel benzoyl urea derivatives having a pryzole group which have active insecticidal properties as an insect growth regulator. The present invention also relates to insecticidal compositions comprising these derivatives and to the use of such compositions for killing and controlling insects.

Several kinds of benzoyl urea compounds have been developed as chitin inhibitors since Dimilin ® was introduced in the market. However most of them have not been commercialized due to their complicated manufacturing processes and high costs even though they have a better effect than Dimilin ®. For example, even though several benzoyl urea derivatives have been synthesized according to the disclosed Japanese Patent laid-open Nos. 85-193960 and 87-178561, and European Patent Nos. 176868 and 52833, these manufacturing processes are too complicated to be improved.

Therefore, with consideration to the foregoing points the present inventors have developed new insecticidal compounds which exhibit broad spectrum and powerful insecticidal activities towards various harmful insects.

Furthermore, they can be prepared via a simple process starting from readily available raw chemicals as compared with existing chitin inhibitor insecticides.

SUMMARY OF THE INVENTION

An object of the present invention is to provide powerful benzoyl urea derivatives with strong insecticidal activities toward various harmful insects and having a simple manufacturing process utilizing raw materials of low cost.

Another object is to provide insecticidal compositions containing active compounds of those derivatives.

DETAILED DESCRIPTION OF THE INVENTION

The present invention is directed to benzoyl urea derivatives having a pyrazole group which correspond to the following formula(I)

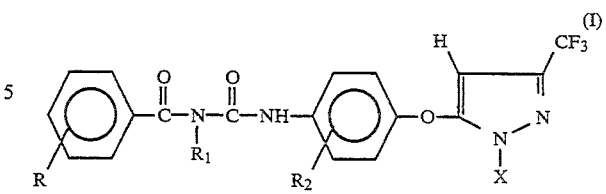

wherein.

R and $R_2$, are the same or different, and are hydrogen, one or more halogen atoms selected from the group consisting of fluorine, chlorine and bromine atoms, a lower alkoxy group or a nitro group:

$R_1$ is a hydrogen atom or a lower alkyl group; and

X is a lower alkyl group or phenyl substituent.

In the present invention, the terms "lower alkoxy group" and "lower alkyl group" designate a straight or branched chain alkoxy and alkyl groups of 1 to 6 carbon atoms.

According to a first embodiment of the present invention, the above benzoyl urea derivatives can be easily prepared by converting substituted benzamide derivatives of the following formula(II) to benzoyl isocyanate of the following formula(III) using oxaryl chloride or phosgene and reacting the compound of formula(III) with anilin derivatives of the following formula(IV) and an acid scavenger.

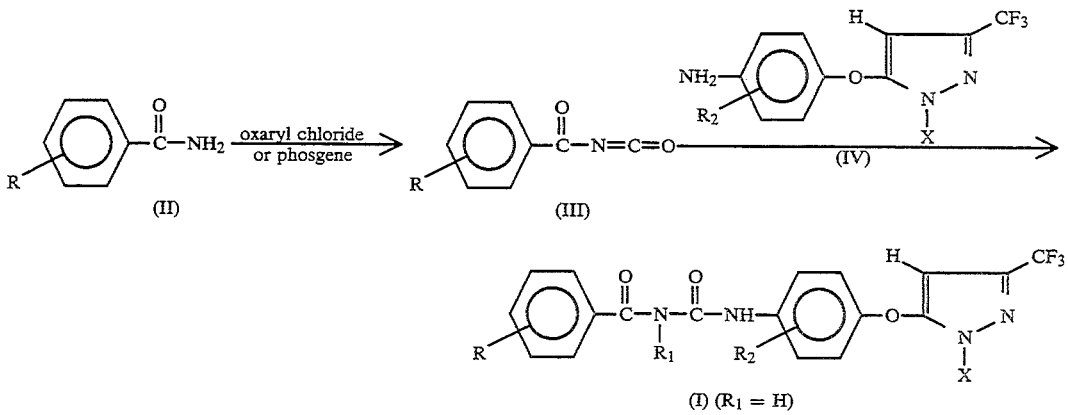

wherein, R, $R_2$ and X are defined as above: and $R_1$ is a hydrogen atom.

In the above reaction, organic solvents such as benzene, toluene, xylene, chlorobenzene or 1,2-dichloroethane can be used for the reaction from substitutied benzamide derivatives of formula(II) to benzoyl isocyanate of formula(III), and then completion of the reaction is assumed when no more gas is produced. Toluene, xylene, chlorobenzene or 1,2-dichloroethane can be used as a solvent for obtaining the desired compound(I) by reacting isocyanate of formula(III) with anilin derivatives of formula(IV), and then 0.5~1 equivalent weight of tertiary amine, e.g. triethyl amine, is used as an acid scavenger.

If the acid scavenger is not added, the yield will be decreased due to coexisting hydrochloride which is produced during the formation of the isocyanate(III). The reaction for the formation of the desired compound(I) is complete when no more anilin derivative remains. This can be easily checked by T.L.C. or G.C.

After completion of the reaction, the desired compound may be separated by well-known methods as follows: the solid compound is obtained by recrystallization after filteration, and the remaining filtrate is washed with water to remove organic solvents, and then the desired compound can be obtained by recrystallization or purified by chromatography and identified by NMR, IR and MS.

Accordingly to a second embodiment, the desired compound(I) can be produced by reacting anilin derivatives of formula(IV) with phosgene to obtain isocyanate of the following formula(V) and adding benzamide derivatives of formula(II) and acid scavenger, according to following reaction scheme.

Typical new benzoyl urea derivatives of formula(I) according to the present invention are listed in Table 1.

TABLE 1

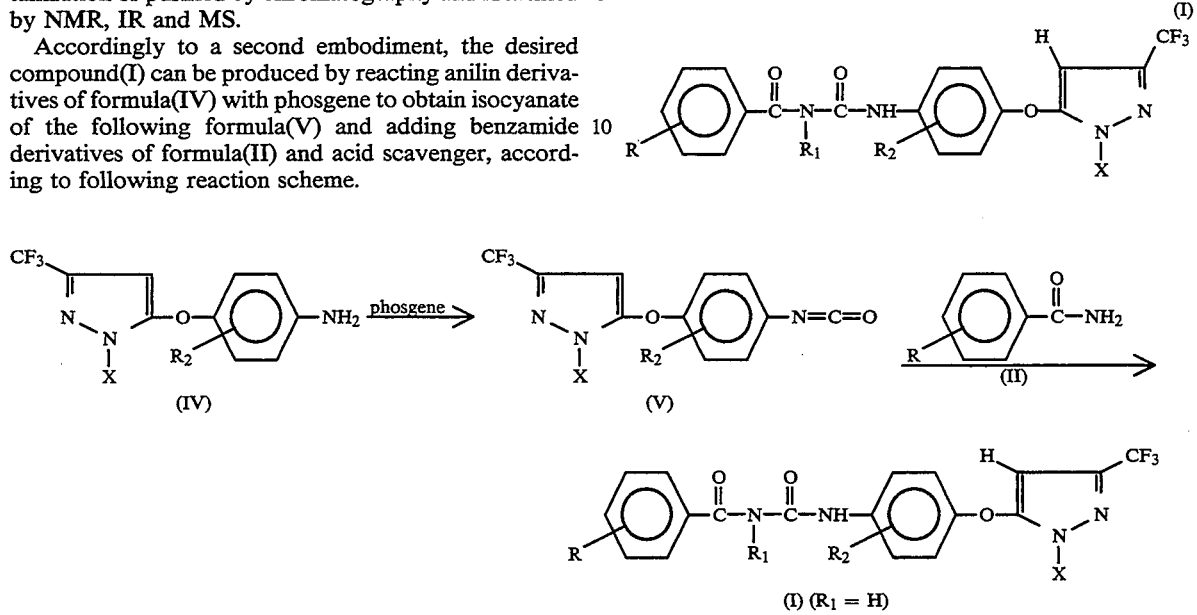

wherein, R, $R_2$ and X are defined as above: and $R_1$ is a hydrogen atom.

In the above reaction, ethylacetate, tetrahydrofuran, benzene, toluene, chlorobenzene, xylene or 1,2-dichloroethane can be used as organic solvent for obtaining the isocyanate compound(V) from the anilin derivatives of formula(IV). The reaction is assumed to be complete when no more hydrogen chloride gas is produced.

Also, toluene, xylene or chlorobenzene can be used as an organic solvent for the reaction of the isocyanate derivatives(V) with the benzamide derivatives(II), and then tertiary amine such as triethylamine can be used as an acid scavenger.

The reaction is assumed to be complete when no more compound of formula(II) remains. The identification of reaction completion, yield and the desired compound is the same as in the above first method.

According to the present invention an alkyl group can be introduced at the $R_1$ position of the desired compound of formula(I) ($R_1$=H) by using alkylating reagent. For example, the compound(I), where $R_1$ is an alkyl group, can be produced by treating methyliodide or ethyliodide with the compound of formula(I)($R_1$=H) and an acid scavenger.

Acetonitrile, dimethylformamide or dimethylsulfoxide may be used as the organic solvent and hydroxides of alkali metal or alkali earth metal, carbonate or tertiary amine may be used as the acid scavenger. The reaction is assumed to be complete when no more compound of formula(I)($R_1$=H) remains, and this can be easily checked by T.L.C. or G.C. After completion of the alkyl substitution reaction, several processes can be applied to obtain the desired compound from the reaction mixture. For example, after washing the reaction mixture with water to remove the used organic solvent, the desired compound can be obtained by recrystalization or chromatography, and it can be confirmed by NMR, IR and MS.

| Compound No. | R | $R_1$ | $R_2$ | X |
|---|---|---|---|---|
| 1 | 2,6-$F_2$ | H | 2,5-$Cl_2$ | $CH_3$ |
| 2 | 2,6-$F_2$ | H | 2,5-$Cl_2$ | phenyl |
| 3 | 2,6-$F_2$ | H | 2-OMe | $CH_3$ |
| 4 | 2,6-$F_2$ | H | 2-$CO_2$Me | $CH_3$ |
| 5 | 2,6-$F_2$ | H | 2,5-$F_2$ | phenyl |
| 6 | 2,6-$F_2$ | H | 3-Cl | $CH_3$ |
| 7 | 2,6-$F_2$ | H | 3-Cl | phenyl |
| 8 | 2,6-$F_2$ | H | 2,3,5,6-$F_2$ | $CH_3$ |
| 9 | 2,6-$F_2$ | H | 2,3,5,6-$F_2$ | phenyl |
| 10 | 2-Cl | H | 2,3,5,6-$F_2$ | phenyl |
| 11 | 2-F | H | 2,3,5,6-$F_2$ | phenyl |

TABLE 1-continued (I)

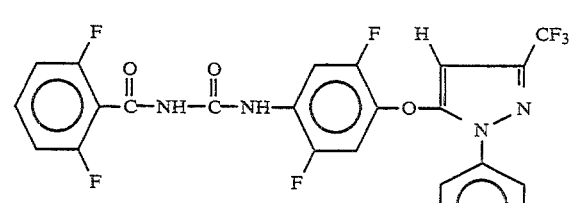

| Compound No. | R | $R_1$ | $R_2$ | X |
|---|---|---|---|---|
| 12 | 2-Cl | H | 2,5-Cl$_2$ | phenyl |
| 13 | 2,6-F$_2$ | H | 3-CF$_3$ | phenyl |
| 14 | 2-Cl | H | 3-CF$_3$ | phenyl |
| 15 | 2-F | H | 3-CF$_3$ | phenyl |
| 16 | 2-Cl | H | 3-Cl | CH$_3$ |
| 17 | 2-F | H | 3-Cl | CH$_3$ |

The present invention is illustrated by following Examples, but should not be construed to be limited thereto.

EXAMPLE 1

Benzamide-2,6-difluoro-N-(((2.5-dichloro-4-(1-methyl-3-trifluoromethyl-5-pyrazoyl-)oxyphenyl)amino)carbonyll (Compound No. 1)

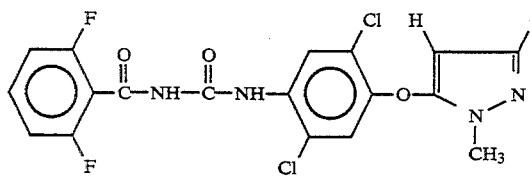

2,6-Difluorobenzamide(0.145 g, 0.92 mmole) and oxarylchloride(0.141 g, 1.11 mmole, 1.2 eq) were added to 1,2-dichloro ethane(6 ml) and the mixture was stirred at 100° C. for 20 hours. 2,5-Dichloro-4-o-(1-methyl-3-trifluormethyl-5-pyrazoyl)-anilin(0.3 g, 0.92 mmole) and triethyl amine(0.664 ml. 0.5 eq) were added and reacted at room temperature for one hour.

Organic solvent was removed under reduced pressure, and then ethyl acetate(60 ml) and water (40 ml) were added to the reaction mixture and the ethyl acetate layer collected, which is dried with anhydrous magnesium sulfate. After removing ethyl acetate under reduced pressure, the desired product (0.311 g, yield 66%) was obtained as a solid by chromatography(ethyl acetate:hexane=1:2).

m.p.: 213°~215° C.

$^1$H NMR(CDCl$_3$+DMSO—d$_6$): δ 3.9(s. 3H), 5.8(s, 1H), 7.0~7.6(m. 4H), 8.6(s. 1H), 11.1(s, 1H), 11.3(s, 1H).

EXAMPLE 2

Benzamide-2,6-difluoro-N-(((2,5-dichloro-4-(1-phenyl-3-trifluoromethyl-5-pyrazoyl)oxyphenyl)amino)carbonyl) (Compound No. 5)

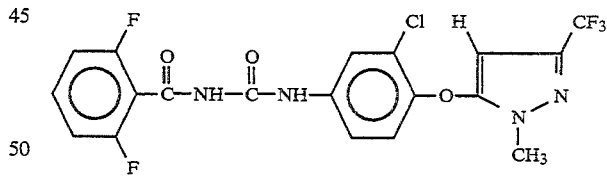

2,6-Difluorobenzamide(0.25 g, 1.59 mmole) and oxarylchloride(0.166 ml, 1.90 mmole, 1.2 eq) were added to 1.2-dichloroethane(6 ml), and the mixture was stirred at 100° C. for 20 hours. 2,5-Difluoro-4-o-(1-phenyl-3-trifluoromethyl-5-pyrazoyl)anilin(0.564 g, 1.59 mmole) and triethylamine(0.11 ml. 0.5 eq) were added and reacted at room temperature for one hour.

Organic solvent was removed under reduced pressure, and then ethyl acetate(80 ml) and water (40 ml) were added to the reaction mixture and the ethyl acetate layer collected, which is dried with anhydrous magnesium sulfate.

After removing ethyl acetate under reduced pressure, the desired product (0.45 g, yield: 52%) was obtained as a solid by recrystallization (ethyl acetate+hexane).

m.p.: 185°~187° C.

$^1$H NMR(CDCl$_3$): δ 5.9(s, 1H), 7.0~8.2(m, 10H), 10.2(s, 1H), 11.0(s, 1H).

EXAMPLE 3

Benzamide-2,6-difluoro-N-(((3-chloro-4-(1-methyl-3-trifluoromethyl-5-pyrazoyl)oxyphenyl)amino)carbonyl) (Compound No. 6)

2,6-Difluoro benzamide(0.25 g, 1.59 mmole) and oxacrylchloride(0.166 ml, 1.90 mmole, 1.2 eq) were added to 1,2-dichloroethane (8 ml), and the mixture was stirred at 100° C. for 20 hours. 3-Chloro-4-o-(1-methyl-3-trifluoromethyl-5-pyrazoyl)-anilin(0.463 g, 1.59 mmole) and triethylamine(0.11 ml, 0.5 eq) were added and reacted at room temperature for one hour.

Organic solvent was removed under reduced pressure, and then ethyl acetate(80 ml) and water (40 ml) were added to the reaction mixture and the ethyl acetate layer collected, which is dried with anhydrous magnesium sulfate.

After removing ethyl acetate under reduced pressure, the desired product(0.377 g, yield: 50%) was obtained as a solid by recrystallization(ethyl acetate+hexane).

m.p.: 193°~195° C.

¹H NMR(CDCl₃): δ 3.8(s. 3H), 5.8(s. 1H), 7.0~7.8(m. 6H), 10.1(s. 1H), 10.8(s. 1H).

EXAMPLE 4

Benzamide-2,6-difluoro-N-(((3-chloro-4-(1-phenyl-3-trifluoromethyl-5-pyrazoyl)oxyphenyl)amino)carbonyl) (Compound No. 7)

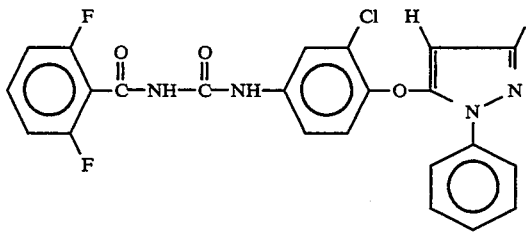

2,6-Difluorobenzamide(0.17 g, 1.131 mmole) and oxarylchloride(0.118 ml, 1.35 mmole, 1.2 eq) were added to 1,2-dichloroethane(6 ml), and the mixture was stirred at 100° C. 20 hours. 3-Chloro-4-o-(1-phenyl-3-trifluoromethyl-5-pyrazoyl)-anilin(0.4 g, 1.131 mmole) and triethylamine(0.09 ml, 0.5 eq) were added and reacted at room temperature for one hour.

Organic solvent was removed under reduced pressure, and then ethyl acetate(70 ml) and water(40 ml) were added to the reaction mixture and the ethyl acetate layer collected, which is dried with anhydrous magnesium sulfate. After removing ethyl acetate under reduced pressure, the desired product(0.31 g, yield: 51%) was obtained as a solid by chromatography(ethyl acetate:hexane =1:5).

m.p.: 169°~172°C.

¹H NMR(CDCl₃) : δ 5.9(s, 1H), 7.0~8.0(m, 1H), 9.8(s, 1H), 10.7(s, 1H).

EXAMPLE 5

Benzamide-2,6-difluoro-N-(((3-chloro-4-(1-phenyl-3-trifluoromethyl-5-pyrazoyl)oxyphenyl)amino)carbonyl) (Compound No. 8)

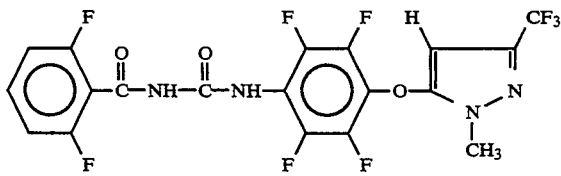

2,6-Difluorobenzamide(0.1 g, 0.636 mmole) and oxarylchloride(0.066 ml, 0.763 mmole, 1.2 eq) were added to 1,2-dichloroethane(6 ml), and the mixture was stirred at 100° C. for 20 hours. 2,3,5,6-Tetrafluoro-4-o-(1-methyl-3-trifluoromethyl-5-pyrazoyl)-anilin(0.209 g, 0.636 mmole) and triethylamine(0.044 ml, 0.5 eq) were added and reacted at room temperature for one hour.

Organic solvent was removed under reduced pressure, and then ethyl acetate(60 ml) and water(30 ml) were added to the reaction mixture and the ethyl acetate layer collected, which is dried with anhydrous magnesium sulfate. After removing ethyl acetate under reduced pressure, the desired product(0.20 g, yield: 61%) was obtained as a solid by chromatography(ethyl acetate:hexane=1:9).

m.p.: 215°~217° C.

¹H NMR(CDCl₃): δ 3.8(s, 3H), 5.8(s, 1H), 6.8~7.6(m, 3H), 9.1(s, 1H), 10.0(s, 1H).

EXAMPLE 6

Benzamide-2,6-difluoro-N-(((2,3,5,6-tetrafluoro-4-(1-phenyl-3-trifluoromethyl-5-pyrazoyl)oxyphenyl)amino)carbonyl) (Compound No. 9)

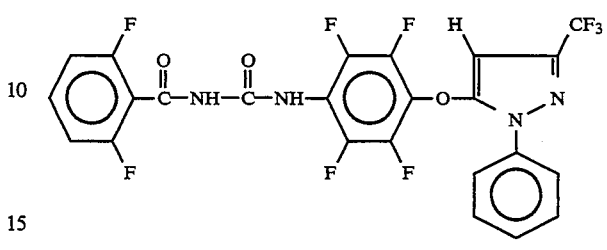

2,6-Difluorobenzamide(0.2 g, 1.27 mmole) and oxarylchloride(0.132 ml, 1.524 mmole, 1.2 eq) were added to 1,2-dichloroethane(8 ml), and the mixture was stirred at 100° C. for 20 hours. 2,3,5,6-Tetrafluoro-4-o-(1-phenyl-3-trifluoromethyl-5-pyrazoyl)-anilin(0.497 g, 1.27 mmole) and triethylamine(0.08 ml, 0.5 eq) were added at room temperature for one hour.

Organic solvent was removed under reduced pressure, and ethyl acetate(70 ml) and water(30 ml) were added to the reaction mixture and the ethyl acetate layer collected, which is dried with anhydrous magnesium sulfate. After removing ethyl acetate under reduced pressure, the desired product(0.45 g, yield : 61%) was obtained as a solid by chromatography(ethyl acetate:hexane=1:9).

m.p. : 198°~200° C.

¹H NMR(CDCl₃) : δ5.9(s, 1H), 6.9°~7.8(m, 8H), 9.4(s, 1H), 10.2(s, 1H)

EXAMPLE 7

Benzamide-2-chloro-N-((2,3,5,6-tetrafluoro-4-(1-phenyl-3-trifluoromethyl-5-pyrazoyl)oxyphenyl)amino)-carbonyl)(Compound No. 10)

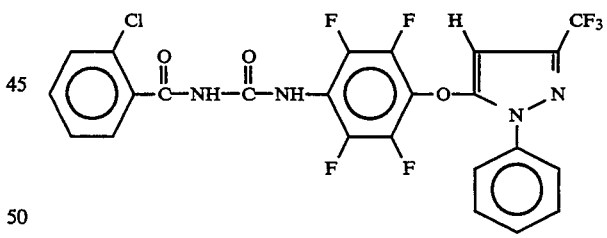

2-Chlorobenzamide(0.1 g, 0.64 mmole) and oxarylchloride(0.067 ml, 0.76 mmole, 1.2 eq) were added to 1,2-dichloroethane(7 ml), and the mixture was stirred at 100° C. for 20 hours. 2,3,5,6-tetrafluoro-4-o-(1-phenyl-3-trifluoromethyl-5-pyrazoyl)-anilin(0.25 g, 0.64 mmole) and triethylamine(0.044 ml, 0.5 eq) were added and reacted at room temperature for one hour.

Organic solvent was removed under reduced pressure, and then ethyl acetate(70 ml) and water(30 ml) were added to the reaction mixture and the ethyl acetate layer collected, which is dried with anhydrous magnesium sulfate. After removing ethyl acetate under reduced pressure, the desired product(0.21 g, yield: 57%) was obtained as a solid by chromatography(ethyl acetate:hexane=1:9).

m.p.: 177°~179° C.

$^1$H NMR(CDCl$_3$): δ 5.9(s, 1H), 7.5~7.9(m, 9H), 9.4(s, 1H), 10.3(s, 1H).

EXAMPLE 8

Benzamide-2-fluoro-N-(((2,3,5,6-tetrafluoro-4-(1-phenyl-3-trifluoromethyl-5-pyrazoyl)oxyphenyl)amino)-carbonyl)(Compound No. 11)

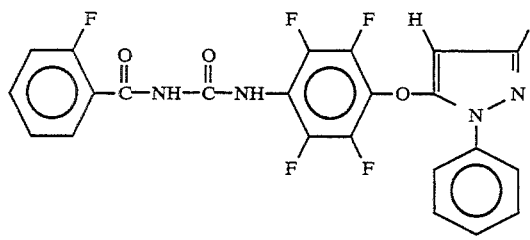

2-Fluorobenzamide(0.088 g, 0.632 mmol and oxarylchloride(0.066 ml, 0.7 were added to 1,2-dichloroethane(7 ml), and the mixture was stirred at 100° C. for 20 hours. 2,3,5,6-Tetrafluoro-4-o-(1-phenyl-3-trifluoromethyl-5-pyrazoyl)-anilin(0.247 g, 0.632 mmole) and triethylamine(0.04 ml, 0.5 eq) were added and reacted at room temperature for one hour.

Organic solvent was removed under reduced pressure, and then ethyl acetate(60 ml) and water(30 ml) were added to the reaction mixture and the ethyl acetate layer collected, which is dried with anhydrous magnesium sulfate. After removing ethyl acetate under reduced pressure, the desired product(0.197 g, yield: 56%) was obtained as a solid by chromatography(ethyl acetate:hexane=1:9).

m.p.: 173°~175° C.

$^1$H NMR(CDCl$_3$): δ 6.0(s, 1H), 7.1~8.2(m, 9H), 9.2(d, 1H), 10.2(s, 1H).

EXAMPLE 9

Benzamide-2-chloro-N-(((3-chloro-4-(1-methyl-3-trifluoromethyl-5-pyrazoyl)oxyphenyl)amino)carbonyl)-(Compound No. 16)

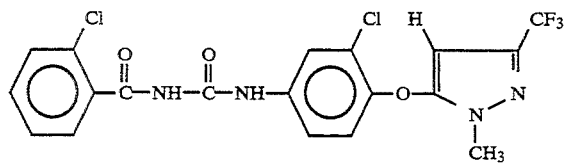

2-Chlorobenzamide(0.25 g, 1.60 mmole) and oxarylchloride(0.168 ml, 1.92 mmole, 1.2 eq) were added to 1,2-dichloroethane(7 ml), and the mixture was stirred at 100° C. for 20 hours. 3-Chloro-4-o-(1-methyl-3-trifluoromethyl-5-pyrazoyl)-anilin(0.468 g, 1.60 mmole) and triethylamine(0.11 ml, 0.5 eq) were added and reacted at room temperature for one hour.

Organic solvent was removed under reduced pressure, and then ethyl acetate(80 ml and water(30 ml) were added to the reaction mixture and the ethyl acetate layer collected, which is dried with anhydrous magnesium sulfate. yield: 65%) was obtained as a solid by chromatography(ethyl acetate:hexane=1:9).

m.p.: 201°~202° C.

$^1$H NMR(CDCl$_3$): δ 4.0(s, 3H), 5.8(s, 1H), 7.3~8.0(m, 7H), 9.9(s, 1H), 10.9(s, 1H).

EXAMPLE 10

Benzamide-2-fluoro-N-(((3-chloro-4-(1-methyl-3-trifluoromethyl-5-pyrazoyl)oxyphenyl)amino)carbonyl)-(Compound No. 17)

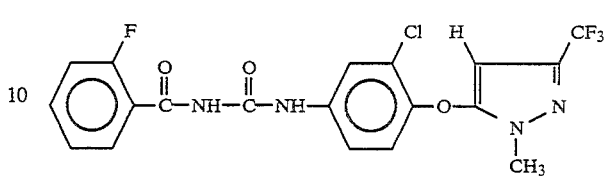

2-Fluorobenzamide(0.143 g, 1.02 mmole) and oxarylchloride(0.107 ml, 1.23 mmole, 1.2 eq) were added to 1,2-dichloroethane(7 ml), and the mixture was stirred at 100° C. for 20 hours. 3-Chloro-4-o-(I-methyl-3-trifluoromethyl-5-pyrazoyl)-anilin(0.3 g, 1.02 mmole) and triethyl amine(0.071 ml, 0.5 eq) were added and reacted at room temperature for one hour.

Organic solvent was removed under reduced pressure, and then ethyl acetate(60 ml) and water (30 ml) were added to the reaction mixture and the ethyl acetate layer collected, which is dried with anhydrous magnesium sulfate. After removing ethyl acetate under reduced pressure, the desired product(0.224 g, yield: 48%) was obtained as a solid by chromatography(ethyl acetate:hexane=1:9).

m.p.: 179°~180° C.

$^1$H NMR(CDCl$_3$): δ 4.1(s, 3H), 5.9(s, 1H), 7.2~8.3(m, 7H), 9.1(d, 1H), 11.0(s, 1H).

EXAMPLE 11

Benzamide-2-chloro-N-(((3-chloro-4-(1-phenyl-3-trifluoromethyl-5-pyrazoyl)oxyphenyl)amino)carbonyl)-(Compound No. 18)

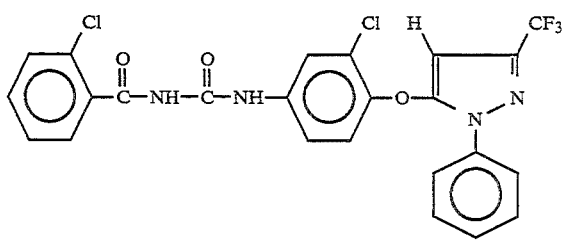

2-Chlorobenzamide(0.132 g, 0.848 mmole) and oxarylchloride (0.088 ml, 1.90 mmole, 1.2 eq) were added to 1,2-dichloromethane(7 ml), and the mixture was stirred at 100° C. for 20 hours. 3-Chloro-4-o-(1-phenyl-3-trifluoromethyl-5-pyrazoyl)-anilin(3 g, 0.848 mmole) and triethylamine(0.059 ml, 0.5 eq) were added and reacted at room temperature for one hour.

Organic solvent was removed under reduced pressure, and then ethyl acetate(80 ml) and water(30 ml) were added to the reaction mixture and the ethyl acetate layer collected, which is dried with anhydrous magnesium sulfate.

After removing ethyl acetate under reduced pressure, the desired product(0.2 g, yield: 44%) was obtained as a solid by chromatography(ethyl acetate:hexane=1:9).

m.p.: 189°~190° C.

$^1$H NMR(CDCl$_3$): δ 5.9(s, 1H), 7.0~8.0(m, 12H), 9.7(s, 1H), 10.8(s, 1H).

EXAMPLE 12

Benzamide-2-chloro-N-(((2,5-difluoro-4-(1-methyl-3-trifluoromethyl-5-pyrazoyl)oxyphenyl)amino)carbonyl)(Compound No. 19)

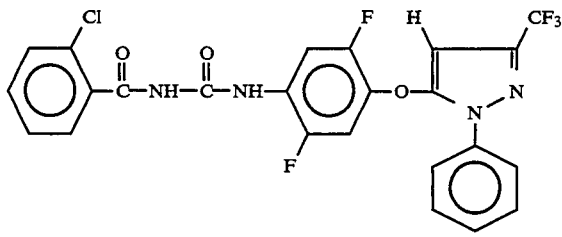

2-Chlorobenzamide(0.131 g, 0.844 mmole) and oxarylchloride(0.088 ml, 1.013 mmole, 1.2 eq) were added to 1,2-dichloroethane(7 ml), and the mixture was stirred at 100° C. for 20 hours. 2,5-Difluoro-4-o-(1-phenyl-3-trifluoro methyl-5-pyrazoyl)-anilin(0.3 g, 0.844 mmole) and triethylamine(0.058 ml. 0.5 eq) were added and reacted at room temperature for one hour.

Organic solvent was removed under reduced pressure, and then ethyl acetate (80 ml) and water(30 ml) were added to the reaction mixture and the ethyl acetate layer collected, which is dried with anhydrous magnesium sulfate.

After removing ethyl acetate under reduced pressure, the desired product(0.2 g, yield : 43%) was obtained as a solid by chromatography(ethyl acetate:hexane=1:9).

m.p.: 181°~182° C.

$^1$H NMR(CDCl$_3$) : δ 5.9(s. 1H), 6.9~8.2(m, 11H), 10(s, 1H), 11.1(s, 1H).

EXAMPLE 13

Benzamide-2,6-difluoro-N-(((2,5-difluoro-4(1-methyl-3-trifluoromethyl-5-pyrazoyl)oxyphenyl)amino)carbonyl) (Compound No. 20)

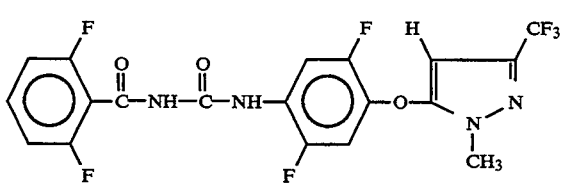

2,6-Difluorobenzamide(0.123 g, 0.784 mmole) and oxarylchloride(0.082 ml, 0.941 mmole, 1.2 eq) were added to 1,2-dichloroethane(7 ml), and the mixture was stirred at 100° C. for 20 hours. 2,5-Difluoro-4-o-(1-methyl-3-trifluoromethyl-5-pyrazoyl)-anilin(0.23 g, 0.784 mmole) and triethyl amine(0.054 ml, 0.5 eq) were added and reacted at room temperature for one hour.

Organic solvent was removed under reduced pressure, and then ethyl acetate(70 ml) and water(30 ml) were added to the reaction mixture and the ethyl acetate layer collected, which is dried with anhydrous magnesium sulfate.

After removing ethyl acetate under reduced pressure, the desired product(0.2 g, yield : 53%) was obtained as a solid by crystallization(ethyl acetate +hexane).

m.p.: 203°~205° C.

$^1$H NMR(CDCl$_3$) : δ 3.8(s, 3H), 5.8(s, 1H), 6.9~8.1(m, 5H), 10.1(s, 1H), 10.8(s, 1H).

EXAMPLE 14

Benzamide-2,6-difluoro-N-(((4-(1-methyl-3-trifluoromethyl-5-pyrazoyl)oxyphenyl)amino)carbonyl) (Compound No. 21)

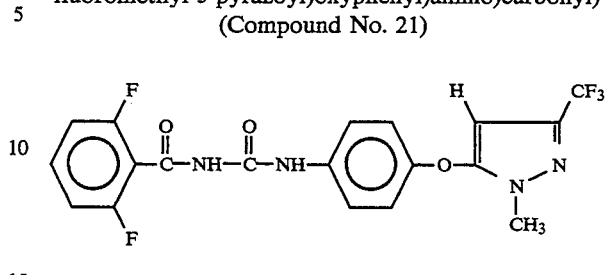

2,6-Difluorobenzamide(0.183 g, 1.16 mmole) and oxarylchloride(0.122 ml, 1.40 mmole, 1.2 eq) were added to 1,2-dichloroethane(7 ml), and the mixture was stirred at 100° C. for 20 hours. 4-o-(1-Methyl-3-trifluoromethyl-5-pyrazoyl)-anilin(0.3 g, 1.16 mmole) and triethylamine(0.08 ml, 0.5 eq) were added and reacted at room temperature for one hour.

Organic solvent was removed under reduced pressure, and then ethyl acetate(70 ml) and water(30 ml) were added to the reaction mixture and the ethyl acetate layer collected, which is dried with anhydrous magnesium sulfate. After removing ethyl acetate under reduced pressure, the desired product (0.303 g, yield : 595) was obtained as a solid by recrystallization(ethyl acetate+hexane).

m.p.: 203° C.

$^1$H NMR(CDCl$_3$) : δ 3.8(s, 3H), 5.8(s, 1H), 6.8~7.5(m, 7H), 9.0(s, 1H), 10.4(s, 1H).

EXAMPLE 15

Benzamide-2,6-difluoro-N-(((3-trifluoromethyl-4-(1-methyl-3-trifluoromethyl-5-pyrazoyl)oxyphenyl)amino)carbonyl) (Compound No. 22)

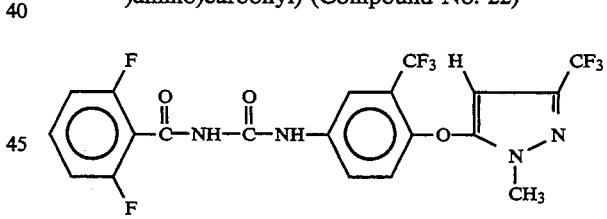

2,6-Difluorobenzamide(0.145 g, 0.922 mmole) and oxarylchloride(0.096 ml, 1.10 mmole, 1.2 eq) were added to 1,2-dichloroethane(6ml), and the mixture was stirred at 100° C. for 20 hours. 3-Trifluoromethyl-4-o-(1-methyl-3-trifluoromethyl-5-pyrazoyl)-anilin(0.3 g, 0.922 mmole) and triethylamine(0.064 ml, 0.5 eq) were added and reacted at room temperature for one hour.

Organic solvent was removed under reduced pressure, and then ethyl acetate(70 ml) and water(30 ml) were added to the reaction mixture and the ethyl acetate layer collected, which is dried with anhydrous magnesium sulfate.

After removing ethyl acetate under reduced pressure, the desired product(0.29 g, yield: 61%) was obtained as a solid by chromatography(ethyl acetate:hexane=1:4).

m.p.: 203° C.

$^1$H NMR(CDCl$_3$): δ 3.8(s, 3H), 5.9(s, 1H), 6.9~7.9(m, 6H), 9.2(s, 1H), 10.7(s, 1H).

EXAMPLE 16

Benzamide-2,6-difluoro-N-(((3,5-dichloro-4-(1-methyl-3-trifluoromethyl-5-pyrazolyl)oxyphenyl)amino)carbonyl) (Compound No. 23)

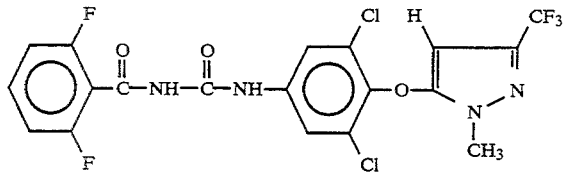

2,6-Difluorobenzamide(0.120 g, 0.766 mmole) and oxarylchloride(0.080 ml, 0.920 mmole, 1.2 eq) were added to 1,2-dichloro ethane(7 ml), and the mixture was stirred at 100° C. for 20 hours. 3,5-Dichloro-4-o-(1-methyl-3-trifluoromethyl-5-pyrazoyl)-anilin(0.25 g, 0.766 mmole) and triethylamine(0.053 ml, 0.5 eq) were added and reacted at room temperature for one hour.

Organic solvent was removed under reduced pressure, and then ethyl acetate(80 ml) and water(30 ml) were added to the reaction mixture and the ethyl acetate layer collected, which is dried with anhydrous magnesium sulfate. After removing ethyl acetate under reduced pressure, the desired product(0.237 g, yield: 61%) was obtained as solid by chromatography(ethylacetate:hexane = 1:5).

m.p.: 221° C.

$^1$H NMR(CDCl$_3$): δ 4.0(s, 3H), 5.6(s, 1H), 7.2~7.6(m, 5H), 10.8(s, 1H).

EXAMPLE 17

Benzamide-2,6-difluoro-N-(((3,5-dichloro-4-(1-phenyl-3-trifluoromethyl-5-pyrazoyl)oxyphenyl)amino)carbonyl) (Compound No. 24)

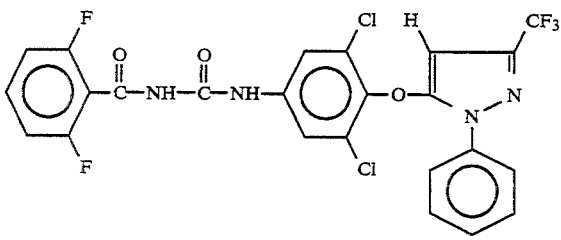

2,6-Difluorobenzamide(0.120 g, 0.766 mmole) and oxarylchloride(0.080 ml, 0.920 mmole, 1.2 eq) were added to 1,2-dichloroethane(7 ml), and the mixture was stirred at 100° C. for 20 hours. 3,5-Dichloro-4-o-(1-phenyl-3-trifluoromethyl-5-pyrazoyl)-anilin(0.297 g, 0.766 mmole) and triethylamine(0.053 ml, 0.5 eq) were added and reacted at room temperature for one hour.

Organic solvent was removed under reduced pressure, and then ethyl acetate(80 ml) and water(30 ml) were added to the reaction mixture and the ethyl acetate layer collected, which is dried with anhydrous magnesium sulfate. After removing ethyl acetate under reduced pressure the desired product(0.274 g, yield: 62%) was obtained as a solid by chromatography(ethylacetate:hexane = 1:5).

m.p.: 236° C.

$^1$H NMR(CDCl$_3$): δ 5.6(s, 1H), 7.0~7.9(m, 10H), 10.2(s, 1H), 10.8(s, 1H).

EXAMPLE 18

Benzamide-2,6-difluoro-N-(((4-(1-phenyl-3-trifluoromethyl-5-pyrazoyl)oxyphenyl)amino)carbonyl) (Compound No. 25)

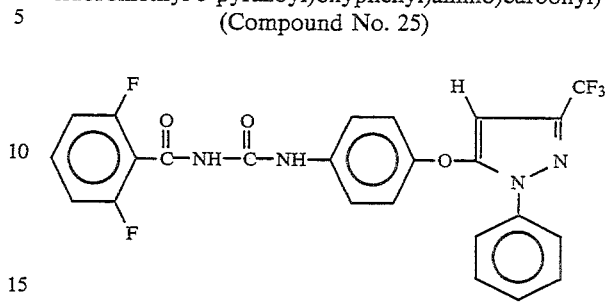

2,6-Difluorobenzamide(0.123 g, 0.783 mmole) and oxarylchloride(0.082 ml, 0.940 mmole, 1.2 eq) were added to 1,2-dichloroethane(7 ml), and the mixture was stirred at 100° C. for 20 hours. 4-o-(1-Phenyl-3-trifluoromethyl-5-pyrazolyl)-anilin(0.25 g, 0.783 mmole) and triethylamine(0.054 ml, 0.5 eq) were added and reacted at room temperature for one hour.

Organic solvent was removed under reduced pressure, and then ethyl acetate(80 ml) and water(30 ml) were added to the reaction mixture and the ethyl acetate layer collected, which is dried with anhydrous magnesium sulfate. After removing under reduced pressure, the desired product(0.25 g, yield=64%) was obtained as a solid by chromatography(ethyl acetate:hexane = 1:5).

m.p.: 215°~218° C.

$^1$H NMR(CDCl$_3$): δ 5.9(s, 1H), 6.9~7.9(m, 12H), 10.5(s, 1H), 10.8(s, 1H).

On the other hand, anilin derivatives of the formula(IV) as raw material used in the present invention may be synthesized by reacting the compound or its salt of formula(VI) with the compound of formula(VII), and then hydrogenolysis of the resulting compound of formula(VIII) as following reaction scheme.

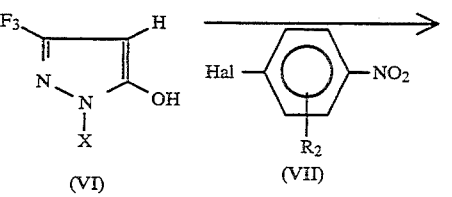

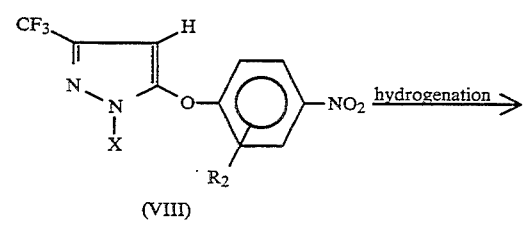

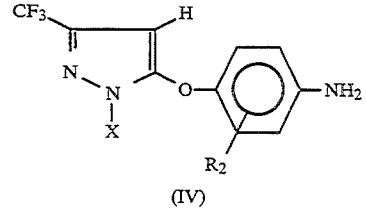

For the reaction of the 5-hydroxy pyrazole compound of formula(VI) with halogen substituted nitrobenzene of formula(VII), common organic solvents such as dimethylformamide, dimethyl sulfoxide, acetonitrile or tetrahydrofuran can be used.

Alkali metal or alkali earth metal, carbonate, percarbonate or tertiary amine can be used as an acid scaprger. The reaction is assumed to be complete when neither of the two starting materials are remains, and this can be easily confirmed by T.L.C. or G.C.

After the completion of the reaction, the compound-(VIII) may be separated by well-known method as follows; for example, the solid compound is obtained by recrystallization after filtering, and the remaining filtrate is washed with water to remove organic solvent, and then the compound(VIII) can be obtained by recrystallization or purfied by chromatography and identified by NMR, IR and MS.

Anilin derivatives of the formula(IV) can be produced by hydrogenolyzing said compound of the formula(VIII) under a metal catalyst such as nickel or paladium with a primary alcohol such as methanol or ethanol being used as the organic solvent.

The reaction is assumed to be completed when no more substituted nitrobenzene compound of formula(-VIII) remains. This can be confirmed by T.L.C. or G.C.

After the completion of hydrogenation, the compound(IV) can be sepaerated and purified as follows; the metal catalyst is removed by filtration, organic solvent is removed, and then the compound(IV) can be obtained by recrystallization or chromatography. They were identified by NRM,IR and MS.

Typical compounds of the formula (VIII) and (IV) as raw materials according to the present invention are listed in Tables 2 and 3 respectively.

TABLE 2

(VIII)

| Compound No. | X | $R_2$ |
|---|---|---|
| 29 | $CH_3$ | 2,5-$Cl_2$ |
| 30 | $CH_3$ | 2,5-$F_2$ |
| 31 | $CH_3$ | 3-Cl |
| 32 | $CH_3$ | 2,3,5,6-$F_4$ |
| 33 | $CH_3$ | 3-$CF_3$ |
| 34 | $CH_3$ | 2-Cl |
| 35 | $CH_3$ | H |
| 36 | $CH_3$ | 3,5-$Cl_2$ |
| 37 | $CH_3$ | 2-OMe |
| 38 | $CH_3$ | 2-$CO_2$Me |
| 39 | Ph | 2,5-$Cl_2$ |
| 40 | Ph | 2,5-$F_2$ |
| 41 | Ph | 3-Cl |

TABLE 2-continued (VIII)

| Compound No. | X | $R_2$ |
|---|---|---|
| 42 | Ph | 2,3,5,6-$F_4$ |
| 43 | Ph | 3-$CF_3$ |
| 44 | Ph | 2-Cl |
| 45 | Ph | H |
| 46 | Ph | 3,5-$Cl_2$ |

TABLE 3

(IV)

| Compound No. | X | $R_2$ |
|---|---|---|
| 47 | $CH_3$ | 2,5-$Cl_2$ |
| 48 | $CH_3$ | 2,5-$F_2$ |
| 49 | $CH_3$ | 3-Cl |
| 50 | $CH_3$ | 2,3,5,6-$F_4$ |
| 51 | $CH_3$ | 3-$CF_3$ |
| 52 | $CH_3$ | 2-Cl |
| 53 | $CH_3$ | H |
| 54 | $CH_3$ | 3,5-$Cl_2$ |
| 55 | $CH_3$ | 2-OMe |
| 56 | $CH_3$ | 2-$CO_2$Me |
| 57 | Ph | 2,5-$Cl_2$ |
| 58 | Ph | 2,5-$F_2$ |
| 59 | Ph | 3-Cl |

TABLE 3-continued (IV)

![Structure IV]

| Compound No. | X | R$_2$ |
|---|---|---|
| 60 | ⬡ | 2,3,5,6-F$_4$ |
| 61 | ⬡ | 3-CF$_3$ |
| 62 | ⬡ | 2-Cl |
| 63 | ⬡ | H |
| 64 | ⬡ | 3,5-Cl$_2$ |

The following are typical reaction conditions for the preparation of the above new compounds shown in Table 2 and Table 3.

EXAMPLE 19

3,5-Dichloro-4-(1-methyl-3-trifluoromethyl-5-pyrazoyl)oxy-nitrobenzene (Compound No. 36)

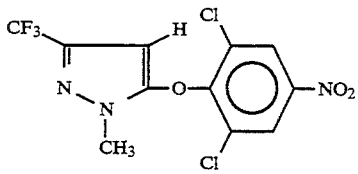

1-Methyl-3-trifluoromethyl-5-hydroxy pyrazole(1 g, 6.02 mmole), 3,4,5-trichloronitrobenzene(1.364 g, 6.02 mmole) and potassium carbonate(1.24 g, 9.03 mmole, 1.5 eq) were added to dimethylformamide(4 ml) and the mixture was stirred at 90°~100° C. for 30 minutes.

Ethyl acetate(80 ml) and water(30 ml) were added and the reaction mixture to ethyl acetate layer collected which is dried with anhydrous magnesium. After removing ethyl acetate under reduced pressure, the desired product(1.5 g, yield: 70%) was obtained as a solid by washing with hexane.

m.p.: 138°~140° C.

$^1$H NMR(CDCl$_3$): δ 3.9(s, 3H), 5.6(s, 1H), 8.3(s, 2H).

EXAMPLE 20

3,5-Dichloro-4-(1-methyl-3-trifluoromethyl-5-pyrazoyl)oxy-anilin(Compound No. 54)

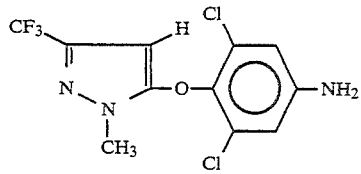

3,5-Dichloro-4-o-(1-methyl-3-trifluoromethyl-5-pyrazoyl)-nitrobenzene (1.4 g, 3.93 mmole) and raney nickel(0.2 g) were added in methanol(30 ml) and reacted under hydrogen gas at 90° C. for 4 hours. The raney nickel was removed by filtration and methanol was removed under reduced pressure, and then the desired product(0.9 g, yield: 70%) was obtained as a solid by chlomatography(ethyl acetate:hexane=1:9).

m.p.: 125° C.

$^1$H NMR(CDCl$_3$): δ 3.8(s, 2H), 3.9(s, 3H), 5.5(s, 1H), 6.6(s, 2H).

Moreover, the present invention is directed to insecticidal compositions comprising the insecticidal compound of the present invention as an active compound. Such insecticidal compositions can be formulated in various forms, such as aqueous dispersions, emulsions, powders, granules and so forth. These compositions are preferred to comprise one or more active compounds of the present invention with one or more suitable adjuvants such as carriers and diluents which are chemically inert to the active compound.

The exact concentration of the active compound in a composition thereof with an adjuvant therefor can vary, it is only necessary that the active compounds be present in sufficient amounts so as to make possible the application of an insecticidally effective dosage.

For example, in the case where the compositions are emulsions or aqueous dispersions, the amount of the active compound is preferred to range from 10 to 90% by weight.

And in the case of powder compositions, the amount is preferred to range from 0.1 to 30% by weight; also in the case of granule compositions, the amount is preferred to range from 1 to 30% by weight. But, the amount of the active compound in the compositions is somewhat variable according to the purpose of use of the compositions.

Preferred carriers to be employed in the compositions according to the present invention are liquid carriers which are selected from alcohols(i.e. monohydric alcohols like methanol, dihydric alcohols like ethyleneglycol, and trihydric alcohols like glycerine, etc.), ketones-(i.e. acetone, methylethylketone, etc.), ethers(i.e. dioxane, tetrahydrofuran, cellosolve, etc.), aliphatic hydrocarbons(i.e. gasoline, kerosene, etc.), hydrocarbon halides (i.e. chloroform, carbon tetrachloride, etc.), acid amides (i.e. dimethylformamide, etc.), esters (i.e. butyl acetate, ethyl acetate, glyceride, etc.), and nitriles (i.e. acetonitrile, etc.), and solid carriers which are selected from mineral particles such as kaolin, clay, bentonite, acid clay, talc, diatomaceous earth, silica and sand, and vegetable powers such as arbor. Said liquid carriers can be used separately or in the company of one or more other liquid carriers.

The insecticidal composition of the present invention may include emulsifying agents, spreaders, dispersing agents or permeating agents. Also, the composition may include noionic, anionic or cationic surfactants, for example, fatty acid soda or polyoxyalkylesters, alkylsulfonates or polyethyleneglycolethers.

On the other hand, one of the compounds of the present invention or compositions containing the same, can be advantageously employed in combination with one or more additional pesticidal compounds which are active agricultural chemicals. Such additional pesticidal compounds may be insecticides, herbicides, plant hormones and sterilizers, and if necessary, fertilizers.

| Composition 1 (Emulsion) | |
|---|---|
| Compound No. 23 | 20% (by weight) |
| xylene | 75% |
| polyoxyethylenglycolether | 5% |

The foregoing components were mixed to form an emulsion composition.

| Composition 2 (Powder) | |
|---|---|
| Compound No. 20 | 5% (by weight) |
| kaoline | 94.6% |
| silicon (antifoaming agent) | 0.3% |
| polyoxyethylenglycolether | 0.1% |

The foregoing components were mixed to form a powder composition.

| Composition 3 (Aqueous dispersion) | |
|---|---|
| Compound No. 24 | 30% (by weight) |
| sodium lignosulfonate | 5% |
| polyoxyethyleneglycolether | 5% |
| bentonite | 60% |

The foregoing components were mixed to form an aqueous dispersion composition.

| Composition 4 (Granules) | |
|---|---|
| Compound No. 19 | 10% (by weight) |
| sodium lignosulfonate | 5% |
| bentonite | 85% |

The foregoing components were kneaded along with water and formed into a granular composition.

To demonstrate the superior effect of the compounds which were prepared in accordance with the present invention, test solutions with 500 ppm were prepared for the first insecticidal tests unless otherwise specified.

The insecticidal rates (%) were calculated from these solutions. In the case of an insecticidal rate of 100%, the concentration of the test solution was gradually reduced until the $LC_{50}$ value, namely the concentration (ppm) which gives an insecticidal rate of 50%, was determined.

This test is illustrated by the following examples, but should not be construed to be limited thereto.

TEST 1

Insecticidal test for Diamond-backmoth

Diamond-backmoths (*Plutella Xylostella Linnaeus*) were successively reared using cabbage, and the third instar larvae thereof were tested. For the insecticidal test, a piece of cabbage leaf 9 cm in diameter was dipped in a test solution for 30 minutes and air-dried for 30 minutes. The dried piece of cabbage leaf was put in a petri dish, and 10 of the third instar larvae were inoculated therein. The petri dish was capped and placed in a incubator. At 120 hours after 24 hours, the number of killed moths was examined to determine the insecticidal rate(%), and then the tested cabbage leaf was replaced with a new one every 48 hours.

The results are shown in Table 4.

TABLE 4

| Compound No. | Insecticidal Rate (%) |
|---|---|
| 2 | 100 |
| 5 | 100 |
| 6 | 100 |
| 7 | 100 |
| 8 | 40 |
| 9 | 80 |
| 10 | 80 |
| 12 | 100 |
| 13 | 100 |
| 14 | 100 |
| 15 | 100 |
| 16 | 100 |
| 17 | 100 |
| 18 | 100 |
| 19 | 100 |
| 20 | 70 |
| 22 | 100 |
| 23 | 100 |
| 24 | 100 |
| 26 | 100 |
| no treatment | 0 |

Those compounds which produced an insecticidal rate of 100% at 500 ppm and, for comparison, commercial insecticidals(controls) were tested according to the method mentioned above, and the $LC_{50}$ values were determined.

The results are shown in Table 5.

TABLE 5

| Compound No. | $LC_{50}$ (ppm) |
|---|---|
| Dimilin (control) | 100~125 |
| Chlorofluazuron (control) | 0.035 |
| 2 | 20 |
| 5 | 2.5 |
| 6 | 20 |
| 7 | 40 |
| 13 | 3 |
| 14 | 10 |
| 16 | 50 |
| 17 | 10 |
| 18 | 5 |
| 19 | 3 |
| 22 | 0.9 |
| 23 | 0.15 |
| 24 | 0.5 |

TEST 2

Insecticidal test for Tobacco cutworm

Tobacco cutworms(*Spodop-tera litura*) were successively reared using cabbage, and the third instar larvae thereof were tested. For the insecticidal test, a piece of cabbage leaf 9 cm in diameter was dipped in a test solution for 30 seconds and air-dried for 30 minutes. The dried piece of cabbage leaf was put in a petri dish 9 cm in diameter, and 10 of the third instar larvae were inoculated therein. The petri dish was placed in an incubator, and at 120 hours, the number of killed cutworms was examined to determine the insecticidal rate(%). The tested cabbage leaf was replaced with a new one every 48 hours.

The results are shown in Table 6.

TABLE 6

| Compound No. | Insecticidal Rate (%) |
|---|---|
| 2 | 100 |
| 5 | 100 |
| 6 | 100 |
| 7 | 100 |
| 8 | 100 |
| 9 | 80 |
| 10 | 80 |
| 11 | 60 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 26 | 100 |
| no treatment | 0 |

Those compounds which produced an insecticidal rate of 100% at 500 ppm and for comparison, commercial insecticidals (controls) were tested according to the method mentioned above, and the $LC_{50}$ values were determined.

The results are shown in Table 7.

TABLE 7

| Compound No. | $LC_{50}$ (ppm) |
|---|---|
| Dimilin (control) | 3.3 |
| Chlorofluazuron (control) | 0.022 |
| 2 | 0.7 |
| 5 | 0.04 |
| 6 | 0.04 |

TABLE 7-continued

| Compound No. | $LC_{50}$ (ppm) |
|---|---|
| 7 | 0.15 |
| 8 | 3.5 |
| 13 | 7 |
| 14 | 1.5 |
| 16 | 5 |
| 17 | 1.5 |
| 18 | 3 |
| 19 | 0.7 |
| 20 | 0.2 |
| 21 | 0.4 |
| 22 | 0.4 |
| 23 | 0.2 |
| 24 | 0.06 |
| 26 | 4 |

From the results of the above test, it is demonstrated that the benzoyl urea derivatives having pyrazole group according to the present invention exhibit excellent bioactivity against Diamond-backmoth and Tobacco cutworm; namely activity similar to chlorfluazuron but superior to Dimilin.

Moreover, the present novel benzoyl urea derivatives can be prepared cheaply via simple processes starting form readily available raw materials as compared to existing high priced chitin inhibitor insecticides.

What is claimed is:

1. An anilin derivative which corresponds to the following formula:

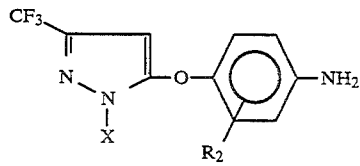

wherein, $R_2$ is hydrogen, lower alkoxy group, a nitro group, or one or more halogen atoms selected from fluorine, chlorine and bromine; and X is a lower alkyl group or a phenyl substituent.

* * * * *

UNITED STATES PATENT AND TRADEMARK OFFICE
CERTIFICATE OF CORRECTION

PATENT NO. : 5,430,158

DATED : 4 July 1995

INVENTOR(S) : Ki J. HWANG et al.

It is certified that error appears in the above-identified patent and that said Letters Patent is hereby corrected as shown below:

| Column | Line | |
|---|---|---|
| 1 | 9 | Change "pryzole" to --pyrazole--. |
| 1 | 27 | Before "broad" insert --powerful--; after "spectrum" delete "and powerful--. |
| 4 | 53 | Change "...$F_2$" to --...$F_4$--. |
| 4 | 54 | Change "...$F_2$" to --...$F_4$--. |
| 4 | 59 | Change "...$F_2$" to --...$F_4$--. |
| 4 | 64 | Change "...$F_2$" to --...$F_4$--. |

UNITED STATES PATENT AND TRADEMARK OFFICE
CERTIFICATE OF CORRECTION

PATENT NO. : 5,430,158

DATED : 4 July 1995

INVENTOR(S) : Ki. J. HWANG et al.

It is certified that error appears in the above-identified patent and that said Letters Patent is hereby corrected as shown below:

Column    Line

5    After 33:    Insert the following:

| Compound No. | R | $R_1$ | $R_2$ | X |
|---|---|---|---|---|
| 18 | 2-Cl | H | 3-Cl | ⊚ |
| 19 | 2-Cl | H | 2,5-$F_2$ | ⊚ |
| 20 | 2,6-$F_2$ | H | 2,5-$F_2$ | $CH_3$ |
| 21 | 2,6-$F_2$ | H | H | $CH_3$ |
| 22 | 2,6-$F_2$ | H | 3-$CF_3$ | $CH_3$ |
| 23 | 2,6-$F_2$ | H | 3,5-$Cl_2$ | $CH_3$ |
| 24 | 2,6-$F_2$ | H | 3,5-$Cl_2$ | ⊚ |
| 25 | 2,6-$F_2$ | H | H | ⊚ |
| 26 | 2,6-$F_2$ | H | 2-Cl | ⊚ |
| 27 | 2,6-$F_2$ | H | 2-Cl | $CH_3$ |
| 28 | 2,6-$F_2$ | $CH_3$ | 3-Cl | $CH_3$ |

UNITED STATES PATENT AND TRADEMARK OFFICE
CERTIFICATE OF CORRECTION

PATENT NO. : 5,430,158
DATED : 4 July 1995
INVENTOR(S) : Ki. J. HWANG et al.

It is certified that error appears in the above-identified patent and that said Letters Patent is hereby corrected as shown below:

| Column | Line | |
|---|---|---|
| 5 | 42 | Change "...carbonyll" to --...carbonyl)--. |
| 8 | 34 | Change "$\delta$ 5.9..." to --$\delta$ 5.9...--. |
| 9 | 63 | After "sulfate." insert --After removing ethyl acetate under reduced pressure, the desired product (0.499g,--. |
| 10 | 18 | Change "...(I-methyl...) to --...(1-methyl...--. |
| 13 | 4 | Change "...pyrazolyl)..." to --...pyrazoyl)...--. |
| 14 | 21 | Change "...pyrazolyl..." to --...pyrazoyl...--. |

UNITED STATES PATENT AND TRADEMARK OFFICE
CERTIFICATE OF CORRECTION

PATENT NO. : 5,430,158

DATED : 4 July 1995

INVENTOR(S) : Ki. J. HWANG et al.

It is certified that error appears in the above-identified patent and that said Letters Patent is hereby corrected as shown below:

| Column | Line | |
|---|---|---|
| 15 | 2 | After "with" insert --the--. |
| 15 | 7 | Change "scaprger" to --scavenger--. |
| 15 | 9 | Delete "are". |
| 15 | 13 | After "follows" change ";" to --:--. |
| 15 | 28 | After "follows" change ";" to --:--. |
| 17 | 61 | Change "and" to --to--; after "mixture" change "to" to --and the--. |
| 18 | 37 | After "vary" change "," to --;--. |
| 19 | 4 | Change "noionic" to --nonionic--. |
| 20 | 5 | Change "a" to --an--. |

UNITED STATES PATENT AND TRADEMARK OFFICE
CERTIFICATE OF CORRECTION

PATENT NO. : 5,430,158

DATED : 4 July 1995

INVENTOR(S) : Ki J. HWANG et al.

It is certified that error appears in the above-identified patent and that said Letters Patent is hereby corrected as shown below:

| Column | Line | |
|--------|------|---|
| 22 | 17 | Change "test" to --tests--. |
| 22 | 24 | Change "form" to --from--. |

Signed and Sealed this

Fourth Day of February, 1997

Attest:

BRUCE LEHMAN

Attesting Officer

Commissioner of Patents and Trademarks